United States Patent [19]
Whitton et al.

[11] Patent Number: 6,018,045
[45] Date of Patent: Jan. 25, 2000

[54] PROCESS FOR PREPARING 4,6-DICHLORO-PYRIMIDINE

[75] Inventors: Alan John Whitton; David John Ritchie, both of Falkirk; Ewan Campbell Boyd, Alloa; Raymond Vincent Heavon Jones, West Lothian, all of United Kingdom

[73] Assignee: Zeneca Limited

[21] Appl. No.: 08/875,896

[22] PCT Filed: Jan. 4, 1996

[86] PCT No.: PCT/GB96/00013

§ 371 Date: Jul. 17, 1997

§ 102(e) Date: Jul. 17, 1997

[87] PCT Pub. No.: WO96/23776

PCT Pub. Date: Aug. 8, 1996

[30] Foreign Application Priority Data

| Jan. 30, 1995 | [GB] | United Kingdom | 9501738 |
| Apr. 13, 1995 | [GB] | United Kingdom | 9507787 |
| May 26, 1995 | [GB] | United Kingdom | 9510751 |

[51] Int. Cl.[7] ................................................ C07D 239/30
[52] U.S. Cl. ............................................................. 544/334
[58] Field of Search ............................................. 544/334

[56] References Cited

U.S. PATENT DOCUMENTS

| 3,845,194 | 10/1974 | Somlo et al. | 423/300 |
| 4,659,827 | 4/1987 | Herd et al. | 544/299 |
| 4,668,788 | 5/1987 | Beitzke et al. | 544/319 |
| 5,352,787 | 10/1994 | Andres et al. | 544/309 |
| 5,525,724 | 6/1996 | Hunds | 544/334 |

FOREIGN PATENT DOCUMENTS

| 1082031 | 2/1994 | China . |
| 0 101 561 | 2/1984 | European Pat. Off. . |
| 0 183 092 | 6/1986 | European Pat. Off. . |
| 0 697 406 | 2/1996 | European Pat. Off. . |
| 0 738 717 | 10/1996 | European Pat. Off. . |
| 0 745 593 | 12/1996 | European Pat. Off. . |
| 0 761 653 | 3/1997 | European Pat. Off. . |
| 91/01310 | 2/1991 | WIPO . |
| 94/07892 | 4/1994 | WIPO . |

OTHER PUBLICATIONS

S. Gronowitz, et al., Chemica Scripta, "On the Synthesis of Various Thienyl– and Selenienylpyrimidines", 1986, 26, 305–309.

J. Chem. Soc. (1943), pp. 574–575, "Experiments on the Synthesis of Purine Nucleosides 4,6–Diaminopyrimidine. A New Synthesis of Pyrimidine Derivatives".

The Pyrimidines, by D.J. Brown [1994 Edition], pp 329–340, John Wiley and Sons.

Bull. Chem. Soc. Japan (1973), vol. 46, pp. 299–302, Yanagida et al., "Studies on Nitrile Salts. II. A Facile One–Step Synthesis of the Pyrimidine Nucleus".

Chemical Abstracts, vol. 122, 81393, 1995.
Chemical Abstracts, vol. 113, 115234, 1990.
Chemical Abstracts, vol. 113, 97564, 1990.
Chemical Abstracts, vol. 113, 78321, 1990.
Chemical Abstracts, vol. 113, 23838, 1990.
Chemical Abstracts, vol. 112, 55765, 1990.
Chemical Abstracts, vol. 111, 57357, 1989.
Chemical Abstracts, vol. 110, 172946, 1989.
Chemical Abstracts, vol. 110, 95143, 1989.
Chemical Abstracts, vol. 107, 23647, 1987.
Chemical Abstracts, vol. 107, 58962, 1987.
Chemical Abstracts, vol. 103, 215248, 1985.
Chemical Abstracts, vol. 104, 19434, 1986.
Chemical Abstracts, vol. 106, 196369, 1987.
Chemical Abstracts, vol. 105, 43176, 1986.
Chemical Abstracts, No. 53, No. 21998, 1959.
Derwent Abstracts, No. 92–309033/38, 1992.
Derwent Abstracts, No. 02846X/02, 1976.

F. Ishikawa et al., Cyclic Guanidines. 17. Novel (N–Substituted amino)imidazo[2,1–b]quinazolin–2–ones: Water-–Soluble Platelet Aggregation Inhibitors, 28 J. Med. Chem. 1387–93 (1985).

*Primary Examiner*—John M. Ford
*Attorney, Agent, or Firm*—David P. LeCroy

[57] ABSTRACT

A process for preparing 4,6-dichloropyrimidine is described, comprising treating 4,6-dihydroxypyrimidine with phosphorus oxychloride in the presence of a saturated hindered amine, the hydrochloride salt of a saturated hindered amine, or an unsaturated 5-membered nitrogen containing ring or a mixture thereof, and, as a first step, directly extracting the 4,6-dichloropyrimidine so formed.

11 Claims, No Drawings

PROCESS FOR PREPARING 4,6-DICHLORO-PYRIMIDINE

The present invention relates to a process for converting 4,6-dihydroxypyrimidine (1) into 4,6-dichloropyrimidine (2). 4,6-Dichloropyrimidine is useful as a chemical intermediate (for example in the agrochemical industry).

It is known that 4,6-dichloropyrimidine can be prepared by reacting 4,6-dihydroxypyrimidine with phosphorus oxychloride in the presence of a suitable base such as dimethylaniline (see Journal Chemical Society (1943) 574–5, and (1951) 2214) or N,N-dimethylcyclohexylamine (or its hydrochloride) or triethylamine hydrochloride (see GB2287466). It is also known that 4,6-dichloropyrimidine can be prepared by reacting 4,6-dihydroxypyrimidine with phosgene in the presence of a suitable base (see WO 95/29166).

The present invention provides a process for preparing 4,6-dichloropyrimidine comprising treating 4,6-dihydroxypyrimidine with phosphorus oxychloride in the presence of a saturated hindered amine, the hydrochloride salt of a saturated hindered amine, or an unsaturated 5-membered nitrogen containing ring or a mixture thereof, and separating 4,6-dichloropyrimidine from the reaction mixture so formed.

Saturated hindered amines include secondary and tertiary amines, particularly amines of formula $R^1R^2R^3N$ wherein $R^1$, $R^2$ and $R^3$ are, independently, $C_{1-10}$ alkyl (especially $C_{1-6}$ alkyl) or $C_{3-6}$ cycloalkyl or $R^1$ and $R^2$ join to form a piperidine or pyrrolidine ring, or $R^3$ may also be hydrogen. Saturated hindered amines include, for example, N,N-diisopropylethylamine $(((CH_3)_2HC)_2(CH_3CH_2)N$, sometimes referred to as Hünig's base, CAS Registry No. 7087-68-5), triethylamine, N,N-diisopropylmethylamine, N,N-diisopropylisobutylamine, N,N-diisopropyl-2-ethylbutylamine, N,N-dicyclohexylmethylamine, N,N-dicyclohexylethylamine, N,N-butylcyclohexylamine, N-methylpyrrolidine or N-ethylpiperidine.

4,6-Dihydroxypyrimidine (1) can also exist in the tautomeric forms (A) and (B) and references to 4,6-dihydroxypyrimidine include all its tautomeric forms.

Unsaturated 5-membered nitrogen containing rings are optionally substituted with $C_{1-6}$ alkyl. The ring preferably comprises 1, 2 or 3 nitrogen atoms and is, for example, imidazole, pyrazole, 1,2,3-triazole or 1,2,4-triazole.

In one aspect the present invention provides a process for preparing 4,6-dichloropyrimidine comprising treating 4,6-dihydroxypyrimidine with phosphorus oxychloride in the presence of either a saturated tertiary amine or an unsaturated 5-membered nitrogen containing ring or a mixture thereof.

A saturated tertiary amine is particularly an amine of formula $R^1R^2R^3N$ wherein $R^1$, $R^2$ and $R^3$ are, independently, $C_{1-10}$ alkyl (especially $C_{1-6}$ alkyl), or $R^1$ and $R^2$ join to form a piperidine or pyrrolidine ring. Saturated tertiary amines include, for example, N,N-diisopropylethylamine, triethylamine, N,N-diisopropylmethylamine, N,N-diisopropylisobutylamine, N,N-diisopropyl-2-ethylbutylamine, N,N-dicyclohexylmethylamine, N,N-dicyclohexylethylamine, N-tert-butylcyclohexylamine, N-methylpyrrolidine or N-ethylpiperidine.

Alkyl groups are straight or branched chain and, unless stated otherwise, preferably contain from 1 to 6, especially from 1 to 4, carbon atoms. Examples are methyl, ethyl, iso-propyl, n-propyl, n-butyl, sec-butyl, iso-butyl and tert-butyl.

Cycloalkyl groups comprise 3 to 6 carbon atoms and are optionally substituted by $C_{1-6}$ alkyl. Examples are cyclohexyl and 2-ethylcyclohexyl.

In another aspect the present invention provides a process for preparing 4,6-dichloropyrimidine comprising treating 4,6-dihydroxypyrimidine with phosphorus oxychloride in the presence of N,N-diisopropylethylamine or diisopropylethylamine hydrochloride.

In a further aspect the present invention provides a process for preparing 4,6-dichloropyrimidine comprising treating 4,6-dihydroxypyrimidine with phosphorus oxychloride in the presence of N,N-diisopropylethylamine.

Unless specified to the contrary below, it is preferred that the molar ratio of phosphorus oxychloride:4,6-dihydroxypyrimidine is in the range 1:1 to 10:1 (especially in the range 2:1 to 4:1).

A mixture of a saturated tertiary amine and unsaturated 5-membered nitrogen containing ring can be used in the process of the invention. If it is used, it is preferred that molar ratio of saturated tertiary amine:unsaturated 5-membered nitrogen containing ring is in the range 100:1 to 1:10 (especially 100:1 to 10:1).

It is preferred that the phosphorus oxychloride:saturated hindered amine, phosphorus oxychloride:saturated hindered amine hydrochloride, phosphorus oxychloride:saturated tertiary amine or phosphorus oxychloride:unsaturated 5-membered nitrogen containing ring molar ratio is in the range 1:10 to 10:1, especially in the range 1:4 to 4:1.

It is preferred that the 4,6-dihydroxypyrimidine:saturated hindered amine, 4,6-dihydroxypyrimidine:saturated hindered amine hydrochloride, 4,6-dihydroxypyrimidine:saturated tertiary amine or 4,6-dihydroxypyrimidine:unsaturated 5-membered nitrogen containing ring molar ratio is in the range 1:5 to 5:1.

It is preferred that the molar ratio of 4,6-dihydroxypyrimidine: phosphorus oxychloride:[saturated hindered amine or saturated hindered amine hydrochloride] is in the range (0.8–1.2):(2–2.5):(1.8–2.2) especially about 1:(2–2.5):2.

The process can be carried out in a solvent or mixture of solvents. Chlorinated solvents (such as dichloromethane or chlorobenzene), saturated or unsaturated hydrocarbons (such as aromatic solvents (for example toluene or a xylene), straight or branched chain hydrocarbons (for example pentane or hexane), or optionally alkyl substituted $C_{5-7}$ cycloalkanes (for example cyclohexane, cyclopentane or methylcyclohexane), ethers (such as tert-butylmethylether, glyme, diglyme, triglyme, tetrahydrofuran or dimethoxyethane) or polar aprotic solvents (such as nitriles (for example acetonitrile)) are preferred. Mixtures of solvents include, for example, a mixture of acetonitrile and dichloromethane. However, the process of the invention can be conducted in the absence of a solvent. Alternatively, an excess of phosphorus oxychloride or, when used, saturated tertiary amine (such as N,N-diisopropylethylamine) can be used as solvent.

The process is preferably carried out in the temperature range 20° C. to 140° C., especially 25° C. to 120° C. (such as 40° C. to 100° C. or 40° C. to 120° C.), particularly 60° C. to 90° C.

In another aspect the present invention provides a process for preparing 4,6-dichloropyrimidine comprising adding phosphorus oxychloride to a mixture of 4,6-dihydroxypyrimidine and a saturated hindered amine (preferably a saturated tertiary amine).

When 4,6-dihydroxypyrimidine, phosphorus oxychloride and the saturated hindered amine, the hydrochloride salt of a saturated hindered amine, or an unsaturated 5-membered nitrogen containing ring or a mixture thereof are mixed a reaction mixture is produced.

In yet another aspect the present invention provides a process for preparing 4,6-dichloropyrimidine the process comprising reacting phosphorus oxychloride with a mixture of 4,6-dihydroxypyrimidine and a saturated hindered amine or hydrochloride thereof (especially a saturated tertiary amine (such as N,N-diisopropylethylamine)) and heating the reaction mixture to a temperature in the range 25° C. to 120° C. (such as 40° C. to 90° C.), particularly in the range 60° C. to 90° C. It is preferred that the amounts of the components used in the process are within the molar ratios expressed above.

In a further aspect the present invention provides a process for preparing 4,6-dichloropyrimidine comprising simultaneous addition of phosphorus oxychloride and 4,6-dihydroxypyrimidine to a saturated hindered amine (particularly a saturated tertiary amine (especially Hünig's base)) or an unsaturated 5-membered nitrogen containing ring or a mixture thereof. It is preferred that the amounts of the components used in the process are within the molar ratios expressed above.

In another aspect the present invention provides a process for preparing 4,6-dichloropyrimidine comprising adding a slurry of 4,6-dihydroxypyrimidine in Hünig's base to phosphorus oxychloride. It is preferred that the amounts of the components used in the process are within the molar ratios expressed above.

In yet another aspect the present invention provides a process for preparing 4,6-dichloropyrimidine comprising adding 4,6-dihydroxypyrimidine to a mixture of Hünig's base and phosphorus oxychloride. It is preferred that the amounts of the components used in the process are within the molar ratios expressed above.

In a further aspect the present invention provides a process for preparing 4,6-dichloropyrimidine comprising adding Hünig's base to a mixture of 4,6-dihydroxypyrimidine and phosphorus oxychloride. It is preferred that the amounts of the components used in the process are within the molar ratios expressed above.

In a still further aspect the present invention provides a process for preparing 4,6-dichloropyrimidine comprising treating 4,6-dihydroxypyrimidine with a mixture of phosphorus oxychloride and phosgene in the presence of a saturated hindered amine (such as a saturated tertiary amine (especially Hünig's base)) or an unsaturated 5-membered nitrogen containing ring or a mixture thereof optionally in the presence of N,N-dimethylformamide as a catalyst. It is preferred that the phosphorus oxychloride:phosgene ratio is in the range 2:1 to 1:100 (especially 2:1 to 1:40, for example 1:1 to 1:10). When a mixture of phosphorus oxychloride and phosgene is used in the process of the present invention it is preferred that the molar ratio of phosphorus oxychloride:4,6-dihydroxypyrimidine is in the range 10:1 to 1:100 (such as 2:1 to 1:100). It is preferred that the molar of 4,6-dihydroxypyrimidine:saturated hindered amine, 4,6-dihydroxypyrimidine:saturated tertiary amine or 4,6-dihydroxypyrimidine:unsaturated 5-membered nitrogen containing ring is in the range 1:5 to 5:1.

In another aspect the present invention provides a process for preparing 4,6-dichloropyrimidine comprising treating 4,6-dihydroxypyrimidine with phosphorus oxychloride and then adding phosphorus pentachloride to the reaction mixture, the process being carried out in the presence of a saturated hindered amine (such as a saturated tertiary amine (especially Hünig's base)) or an unsaturated 5-membered nitrogen containing ring or a mixture thereof.

During the process of the present invention phosphorus oxychloride chlorinates 4,6-dihydroxypyrimidine to leave phosphorus residues. These residues may be converted back to phosphorus oxychloride by reacting them with phosphorus pentachloride or a mixture of phosphorus trichloride and chlorine. (See, for example, the disclosures in U.S. Pat. No. 3,845,194 and WO94/14774.)

Thus, in a further aspect the present invention provides a process for preparing 4,6-dichloropyrimidine comprising treating 4,6-dihydroxypyrimidine with phosphorus oxychloride and then adding a mixture of phosphorus trichloride and chlorine to the reaction mixture, the process being carried out in the presence of a saturated hindered amine (such as a saturated tertiary amine (especially Hünig's base)) or an unsaturated 5-membered nitrogen containing ring or a mixture thereof.

In another aspect the present invention provides a process for preparing 4,6-dichloropyrimidine comprising the steps: (a) treating 4,6-dihydroxypyrimidine with phosphorus oxychloride in the presence of a saturated hindered amine (such as a saturated tertiary amine (especially Hünig's base)), a saturated hindered amine hydrochloride or an unsaturated 5-membered nitrogen containing ring or a mixture thereof; (b) separating 4,6-dichloropyrimidine from the reaction mixture; and, (c) regenerating phosphorus oxychloride by treating the phosphorus residues from the reaction mixture with either phosphorus pentachloride or a mixture of phosphorus trichloride and chlorine.

In a further aspect the present invention provides a process for preparing 4,6-dichloropyrimidine comprising the steps: (a) treating 4,6-dihydroxypyrimidine with phosphorus oxychloride in the presence of either a saturated tertiary amine (especially Hünig's base) or an unsaturated 5-membered nitrogen containing ring or a mixture thereof; (b) separating 4,6-dichloropyrimidine from the reaction mixture; and, (c) regenerating phosphorus oxychloride by treating the phosphorus residues from the reaction mixture with either phosphorus pentachloride or a mixture of phosphorus trichloride and chlorine.

In another aspect the present invention provides a process as hereinbefore described comprising the steps: (a) treating 4,6-dihydroxypyrimidine with phosphorus oxychloride in the presence of a saturated hindered amine, a saturated hindered amine hydrochloride or an unsaturated 5-membered nitrogen containing ring or a mixture thereof; (b) treating the mixture formed in step (a) with either phosphorus pentachloride or a mixture of phosphorus trichloride and chlorine; (c) adding 4,6-dihydroxypyrimidine and a saturated hindered amine, a saturated hindered amine hydrochloride or an unsaturated 5-membered nitrogen containing ring or a mixture thereof to the mixture formed in step (b); and, (d) separating 4,6-dichloropyrimidine from the reaction mixture.

In yet another aspect the present invention provides a process as hereinbefore described comprising the steps: (a) treating 4,6-dihydroxypyrimidine with phosphorus oxychloride in the presence of a saturated hindered amine, a saturated hindered amine hydrochloride or an unsaturated 5-membered nitrogen containing ring or a mixture thereof; (b) treating the mixture formed in step (a) with either phosphorus pentachloride or a mixture of phosphorus trichloride and chlorine; (c) adding 4,6-dihydroxypyrimidine and a saturated hindered amine, a saturated hindered amine hydrochloride or an unsaturated 5-membered nitrogen containing ring or a mixture thereof to the mixture formed in step (b); (d) optionally repeating steps (b) and (c) once more or two or more (especially 2, 3 or 4)

times; and (e) separating 4,6-dichloropyrimidine from the reaction mixture.

In a still further aspect the present invention provides a process for preparing 4,6-dichloropyrimidine, as hereinbefore described, in which less than one equivalent (for example about half an equivalent) of phosphorus oxychloride is used in the reaction mixture initially, and either phosphorus pentachloride or a mixture of phosphorus trichloride and chlorine (preferably a mixture of phosphorus trichloride and chlorine) is added during the process to regenerate phosphorus oxychloride.

In another aspect, and especially when the process of the invention is carried out as a melt, 4,6-dichloropyrimidine is separated from the reaction mixture by a direct extraction technique (that is it is extracted directly from the reaction mixture) (for example using an exhaustive extraction technique such as counter-current extraction). It is preferred to conduct the direct extraction at an elevated temperature such as a temperature in the range 60–90° C. (especially about 80° C.). Solvents suitable for such direct extractions should be poor solvents for the phosphorus residues produced by the reaction and should have a boiling point such that the solvent and the 4,6-dichloropyrimidine can be easily separated by distillation. Suitable solvents include saturated or unsaturated hydrocarbons (such as aromatic solvents (for example toluene or a xylene), straight or branched chain hydrocarbons (for example pentane, hexane or heptane), or optionally alkyl substituted $C_{5-7}$ cycloalkanes (for example cyclohexane, cyclopentane or methylcyclohexane)), ethers (such as methyltert-butylether), halogenated aromatics (such as halobenzenes (for example chlorobenzene or fluorobenzene)). The choice of an appropriate solvent enables the isolation of high quality 4,6-dichloropyrimidine directly from the reaction mixture. Preferred solvents are saturated hydrocarbons (such as straight or branched chain hydrocarbons (for example pentane, hexane or heptane), or optionally alkyl substituted $C_{5-7}$ cycloalkanes (for example cyclohexane, cyclopentane or methylcyclohexane)). It is particularly preferred that the solvent is methylcyclohexane.

The residue remaining after such a direct extraction may be mixed with an appropriate amount of an aqueous solution of sodium or potassium hydroxide to liberate the saturated hindered amine or unsaturated 5-membered nitrogen containing ring or mixture thereof used in the process and this can be separated using standard techniques. When a saturated hindered amine (especially Hünig's base) is used in the process of the present invention it is preferred that the residue is added to a hot solution of sodium or potassium hydroxide as the heat generated during the addition of the residue may be utilised to cause the saturated hindered amine to boil out of the aqueous mixture (that is to distill out of the mixture).

In yet another aspect 4,6-dichloropyrimidine is separated from the reaction mixture by drowning out the reaction mixture with a mixture of water and organic solvent (especially an aromatic solvent (for example toluene or a xylene), a straight or branched chain hydrocarbon (for example pentane or hexane), or an optionally alkyl substituted $C_{5-7}$ cycloalkane (for example cyclohexane, cyclopentane or methylcyclohexane) and maintaining the pH in the range 1–5 by addition of an aqueous solution of a suitable base (such as an alkali or alkaline earth metal hydroxide or carbonate, for example sodium or potassium hydroxide). Once any residual phosphorus oxychloride, or by-products thereof, have been hydrolysed the mixture is adjusted to pH in the range 3–5 and 4,6-dichloropyrimidine recovered from the organic solvent.

The saturated hindered amine (preferably a saturated tertiary amine) or unsaturated 5-membered nitrogen containing ring used in the process of the present invention can be recovered and reused. For example, the saturated hindered amine (preferably saturated tertiary amine (especially N,N-diisopropylethylamine)) or unsaturated 5-membered nitrogen containing ring can be recovered from the reaction mixture by mixing the reaction mixture with water (preferably keeping the pH between 1 and 5 by addition of an aqueous solution of a suitable base (such as an alkali or alkaline earth metal hydroxide or carbonate, for example sodium or potassium hydroxide)), adjusting (by the addition of a water soluble base, such as an alkali or alkaline earth metal hydroxide or carbonate, for example sodium or potassium hydroxide) the pH of the aqueous phase to within the range 8–14, preferably 9–12, and then:

a. extracting the saturated hindered amine (preferably saturated tertiary amine) or unsaturated 5-membered nitrogen containing ring and 4,6-dichloropyrimidine with an organic solvent [(especially an aromatic solvent (for example toluene or a xylene), a straight or branched chain hydrocarbon (for example pentane or hexane), or an optionally alkyl substituted $C_{5-7}$ cycloalkane (for example cyclohexane, cyclopentane or methylcyclohexane)]. The amine or nitrogen containing ring and 4,6-dichloropyrimidine extracted can then be separated by distillation; or b. when the saturated hindered amine (preferably saturated tertiary amine) or unsaturated 5-membered nitrogen containing ring is a liquid and substantially immiscible with water (for example when N,N-diisopropylethylamine is used), separating 4,6-dichloropyrimidine and the saturated hindered amine (preferably saturated tertiary amine) or unsaturated 5-membered nitrogen containing ring from the pH adjusted aqueous phase. In this circumstance it could well be that the separated amine or nitrogen containing ring includes a proportion of 4,6-dichloropyrimidine. These components can be separated using conventional techniques; or c. when the saturated hindered amine (preferably saturated tertiary amine) or unsaturated 5-membered nitrogen containing ring has a suitable boiling point, distilling the saturated hindered amine (preferably saturated tertiary amine) or unsaturated 5-membered nitrogen containing ring and the 4,6-dichloropyrimidine from the pH adjusted aqueous phase.

The following Examples illustrate the invention. Throughout the Examples the abbreviation hplc means high pressure liquid chromatography.

EXAMPLE 1

To a stirred suspension of 4,6-dihydroxypyrimidine (10.0 g, 89.2 mmol) in N,N-diisopropylethylamine (23.1 g, 30.6 ml, 178 mmol) under a nitrogen atmosphere and cooled with an ice/water bath, was added in portions over 10 minutes, phosphorus oxychloride (34.2 g, 20.8 ml, 223 mmol). When the addition was complete the mixture was stirred for 5 minutes at 5° C. and allowed to come to room temperature (over 15 minutes) before heating to 60° C. (When the mixture reached approximately 60° C. a highly exothermic reaction occurred elevating the temperature to 120° C., heating was removed until the temperature had reached 60° C.) After 2 hours (from the beginning of heating) the reaction mixture was allowed to cool to room temperature, poured into ice/water with stirring and extracted with dichloromethane (100 ml) then (2×80 ml). The combined organic extracts were washed with water (3×70 ml), dried over magnesium sulphate and the solvent evaporated in vacuo (rotory evaporator) to give 4,6-dichloropyrimidine as a pale brown solid (12.3 g; 90% by weight).

The combined aqueous extract and washings were adjusted to pH 14 with 30% aqueous sodium hydroxide solution (60 ml) and extracted with dichloromethane (3×70 ml). The combined organic extract was washed with water (2×70 ml), dried over magnesium sulphate and the solvent evaporated in vacuo to give N,N-diisopropylethylamine as pale yellow liquid 18.5 g.

EXAMPLE 2

To a stirred suspension of 4,6-dihydroxypyrimidine (10.0 g, 89.2 mmol) in N,N-diisopropylethylamine (23.1 g, 30.6 ml, 178 mmol) under a nitrogen atmosphere and the ice/water cooling, was added in portions, phosporus oxychloride (34.2 g, 20.8 ml, 223 mmol). When the addition was complete the cooling bath was removed and the mixture allowed to come to 25° C. (over 15 minutes). Heating was introduced and the temperature brought to 60° C. (When the temperature of the oil bath reached 55° C. a highly exothermic event occurred taking the temperature to 128° C.). The reaction temperature was allowed to fall to 60° C. and then heating continued for a further 105 minutes. (Total heating time 2 hours.) The mixture was cooled to room temperature, poured into ice and water (ca.100 ml) and extracted with dichloromethane (120 ml) then (2×80 ml). The combined organic extract was washed with water (3×70 ml), dried over magnesium sulphate and the solvent evaporated in vacuo to give 4,6-dichloropyrimidine as a brown solid 14.67 g.

The combined aqueous extract and washings were adjusted to pH 9 with 30% aqueous sodium hydroxide and distilled (bath 140° C., distillate 85 to 100° C.) to give 21 ml of N,N-diisopropylethylamine. The pH of the distillation solution was taken to pH 14 (it had fallen to pH 6) and the distillation continued (89 to 100° C.) to give a further portion of N,N-diisopropylethylamine. (Total yield 31 ml of N,N-diisopropylethylamine 80% pure).

EXAMPLE 3

A mixture of 4,6-dihydroxypyrimidine (5.0 g, 44.6 mmol), imidazole (6.07 g, 89.2 mmol) and phosphorus oxychloride (20 ml) was stirred at about 65° C. for three hours under a nitrogen atmosphere. (Most of the solid had gone into solution after 1 hour.) The mixture was then cooled to room temperature, at which point it was semi-solid, and dichloromethane (15 ml) added to give a mobile sludge which was poured into ice/water and stirred for 15 minutes. The mixture was extracted with dichloromethane (3×80 ml), the combined organic extract dried over magnesium sulphate and the solvent evaporated in vacuo to give 4,6-dichloropyrimidine as a pale yellow solid (6.18 g).

EXAMPLE 4

To N,N-diisopropylethylamine (23.0 g, 31.0 ml 175 mmol) under a nitrogen atmosphere and at room temperature was added phosphorus oxychloride (26.7 g, 16.26 ml, 174 mmol) over 5 minutes. When the addition was complete the mixture was stirred for a further 5 minutes. 4,6-Dihydroxypyrimidine (10.0 g, 87.6 mmol) was charged slowly, that is 1 g every 5 minutes, and at the end of the addition, the temperature of the reaction mixture had reached approximately 65° C. The reaction mixture was warmed to 65° C. where a slight exothermic reaction occurred over 10 minutes raising the temperature to approximately 75° C., and within 5 minutes the temperature had dropped to 65° C. After 3 hours (from beginning of heating) the reaction mixture was allowed to cool to 40° C., poured into ice/water (200 ml) with stirring and extracted with dichloromethane (3×150 ml). The combined organic extracts were washed with water (3×100 ml), dried over magnesium sulphate and the solvent evaporated in vacuo (rotary evaporator) to give 4,6-dichloropyrimidine as a pale brown solid (12.18 g).

EXAMPLE 5

To a stirred mixture of N,N-diisopropylethylamine (57.1 g) and phosphorus oxychloride (74.7 g) in methylcyclohexane (25 g, containing 1.96 g 4,6-dichloropyrimidine) under nitrogen and at 75–80° C. was added 4,6-dihydroxypyrimidine (25.0 g) portionwise (that is 1–2.5 g per portion) over about 50 minutes, such that the temperature of the reaction mixture was kept in the range 75–90° C. (exothermic reaction). When the addition was complete the reaction mixture was kept at 75–80° C. for 2 hours. The reaction mixture was then drowned into water (125 ml). (Exothermic reaction; temperature of aqueous layer maintained above 30° C.)

The drowned reaction mixture was added to a stirred mixture of water (125 ml) and methylcyclohexane (90 g, containing 2.3 g 4,6-dichloropyrimidine) and the temperature was maintained between 40° C. and 50° C. during the addition by the addition of ice. The pH of the resulting mixture was adjusted to 5–5.5 by the addition of aqueous potassium hydroxide solution (50% w/w). The mixture was stirred for 20 minutes and the organic (methylcyclohexane) layer was separated from the aqueous layer whilst hot. The solvent was distilled from the organic layer to give 4,6-dichloropyrimidine (30.96 g).

Methylcyclohexane (25 g) was added to the aqueous layer to give a two layer system. Aqueous potassium hydroxide (50% w/w) was added with stirring until the pH of the aqueous layer was in the range 9–10.5. At this point an appreciable amount of N,N-diisopropylethylamine was in the upper, organic layer.

EXAMPLE 6

To a stirred suspension of 4,6-dihydroxypyrimidine (26.06 g, 0.226 mol) in phosphorus oxychloride (76.1 g, 0.496 mol) at 62° C. was added, dropwise and over 25 minutes to maintain the temperature at 70–78° C., N,N-diisopropylethylamine (58.6 g, 0.451 mol). When the addition was complete, the mixture was heated to 85° C. with stirring. After 2 hours the mixture was extracted with methylcyclohexane (3×300 ml). The combined organic extracts contained 4,6-dichloropyrimidine (30.15 g).

EXAMPLE 7

To a stirred mixture of N,N-diisopropylethylamine (230 g, 1.75 mol) and phosphorus oxychloride (298.5 g, 1.93 mol) in methylcyclohexane (100 g) at 80° C. was added, portionwise over 70 minutes to maintain the temperature at 80–92° C., 4,6-dihydroxypyrimidine (100 g). When the addition was complete, the temperature was maintained at 80–84° C. with stirring for 2 hours. The reaction mixture was drowned out into a mixture of water (500 g) and methylcyclohexane (260 g). The pH was maintained in the range 1–5 using 47% aqueous sodium hydroxide solution, and the temperature was maintained below 60° C. After the phosphorus oxychloride had been hydrolysed the pH was adjusted to pH4.5 using 47% aqueous sodium hydroxide solution, the temperature was increased to 80° C. and the aqueous layer was separated and retained (for recovery of N,N-diisopropylethylamine). Analysis showed the organic layer to be 22.21% 4,6-dichloropyrimidine.

The aqueous layer was mixed with methylcyclohexane (100 g), adjusted to pH10 with 47% aqueous sodium hydroxide solution and the resulting mixture was heated to 80° C. with stirring. Agitation was stopped and the mixture settled. The aqueous layer was discharged and the organic layer was washed with water (2×200 ml). Analysis showed the organic layer to contain N,N-diisopropylethylamine (65.6%).

EXAMPLE 8

To phosphorus oxychloride (15.2 g, 99 mmol) was added 4,6-dihydroxypyrimidine (5 g, 45 mmol) with stirring under a nitrogen atmosphere. The slurry was heated to 65° C. and N,N-diisopropylethylamine (Hünig's Base, 11.6 g, 90 mmol) was added dropwise so as to maintain a temperature of less than 80° C. On complete addition, the reaction mixture was heated to 80° C. for 90 minutes. Phosphorus pentachloride (18.7 g, 90 mmol) was added in one portion and the reaction mixture stirred for 30 minutes at 80° C. To the resultant brown liquid was added 4,6-dihydroxypyrimidine (10 g, 90 mmol) in one portion followed by N,N-diisopropylethylamine (23.3 g, 180 mmol) added dropwise such that the temperature was kept below 80° C. On completing the addition, the reaction mixture was held at 80° C. for 90 minutes. Further phosphorus pentachloride (37.5 g, 180 mmol) was added in one portion and the resulting mixture was heated at 80° C. for 30 minutes. To the reaction mixture was added 4,6-dihydroxypyrimidine (20 g, 180 mmol) followed by N,N-diisopropylethylamine (46.5 g, 360 mmol) dropwise. On complete addition, the reaction mixture was stirred at 80° C. for a further 90 minutes.

The hot reaction mixture was then extracted into methylcyclohexane (3×300 g) at 80° C. The extracts were combined and the solvent removed in vacuo to leave 4,6-dichloropyrimidine as a pale brown solid (32.8 g, 70%).

EXAMPLE 9

To an aqueous solution of sodium hydroxide (pH 10–12) at 70° C. were added sequentially phosphorus/N,N-diisopropylethylamine residues (148 g in ca. 15 g aliquots, residues were from a process carried out under conditions analogous to those employed in Example 8) and 47% sodium hydroxide so as to maintain a pH above 9. The exothermic nature of the additions enabled a significant amount of N,N-diisopropylethylamine to be distilled from the batch without the use of external heating. An oil bath was used to drive the distillation to completion (still head temperature of 100° C.). The mixed distillate (water/N,N-diisopropylethylamine) was allowed to settle and the lower water layer was separated and discarded to leave N,N-diisopropylethylamine.

EXAMPLE 10

A mixture of phosphorus oxychloride (74.58 g, 0.48 mol) and 4,6-dihydroxypyrimidine (25.0 g, 0.22 mol) under a nitrogen atmosphere was warmed to 55–60° C. and N,N-diisopropylethylamine (Hünigs Base) (56.92 g, 0.438 mol) added at such a rate that the temperature was maintained around 74° C. (ca. 1 hour). The resulting dark brown reaction mixture was heated at 80° C. for 90 minutes; methylcyclohexane (200 ml) was added and stirring continued for a further 15–20 minutes. The methylcyclohexane layer was separated and the extraction process repeated with two further 200 ml portions of methylcyclohexane. The combined organic extract was evaporated to dryness (rotary evaporator) to give 4,6-dichloropyrimidine as an off-white solid (34.0 g, 97.2% pure, 100% yield).

The extraction residue was cooled to 50° C. and phosphorus pentachloride (62.41 g, 0.285 mol) added over 10 minutes. The mixture was heated at 80° C. for 30 minutes, stirred at room temperature overnight and then vacuum distilled (55° C., 150 mmHg to 90° C., 50 mmHg) to give phosphorus oxychloride (56.52 g, 83% pure).

EXAMPLE 11

To a stirred suspension of 4,6-dihydroxypyrimidine (5.0 g, 44.6 mmol) in N,N-diisopropylethylamine (11.5 g, 82.9 mmol) at room temperature and under a nitrogen atmosphere was added phosphorus oxychloride (6.8 g, 4.2 ml, 44.6 mmol). The mixture was brought to 60° C. for 20 minutes at which time a viscous dark brown liquid had formed. Phosphorus pentachloride (4.6 g, 22.3 mmol) was added in two portions (5 minute gap) and the reaction mixture stirred at 80° C. for 90 minutes. The resulting viscous oil was cooled to ca. 35° C. and poured into ice/water (400 ml); the flask was rinsed with water and dichloromethane (20 ml of each). The combined quench and washings were extracted with dichloromethane (120 ml) then (2×80 ml). The organic extracts were combined, washed with water (3×70 ml), dried over magnesium sulphate and the solvent evaporated in vacuo to give 4,6-dichloropyrimidine as an orange/brown solid (6.85 g),(95.7% strength, 98.6% yield).

EXAMPLE 12

To phosphorus oxychloride (4.39 g, 29 mmol) at room temperature and under a nitrogen atmosphere was added, in one portion, Hünigs base hydrochloride (4.18 g, 25 mmol). The mixture was heated to 80° C. and produced a clear viscous mixture. 4,6-Dihydroxypyrimidine (1.4 g, 13 mmol) was added in three portions (5 minute gap) and the resulting mixture was stirred for 2.5 hours at 80° C. Methylcyclohexane (25 ml) was added, the mixture was stirred vigorously for 20 minutes (80° C.) and then separated. The process was repeated with two further 25 ml portions of methylcyclohexane. The organic extracts were combined and evaporated in vacuo to give 4,6-dichloropyrimidine as a white amorphous solid (1.23 g), (96.6% strength, 62% yield).

To a stirred mixture of the residue remaining after the methylcyclohexane extractions and phosphorus oxychloride (4.13 g, 26 mmol) at 80° C. and under a nitrogen atmosphere was added in one portion 4,6-dihydroxypyrimidine (1.37 g, 12 mmol). The resulting mixture was stirred for 3.5 hours at 80° C. after which methylcyclohexane (25 ml) was added. Stirring was continued for 1 hour and then the layers separated (at 80° C.). The reaction was extracted with two more 25 ml portions of methylcyclohexane (each one was stirred for 20 minutes at 80° C. before separation). The organic extracts were combined and evaporated in vacuo to leave 4,6-dichloropyrimidine as a white solid (1.07 g), (95.8% strength, 55% yield).

EXAMPLE 13

4,6-Dihydroxypyrimidine (25 g) and phosphorus oxychloride (74.6) were charged to a 250 ml three-necked flask fitted with a mechanical stirrer, thermometer, reflux condenser (to scrubber) and pressure equalising dropping funnel (with nitrogen bleed) and the mixture was heated to 60° C.

Hünig's base (57.0 g) was charged to the dropping funnel and added slowly to keep the reaction temperature in the region 80–85° C. After complete addition the reaction mixture was maintained at 80–85° C. for 2 hours. The mixture was transferred to a jacketed separating funnel and mixed with methylcyclohexane (300 g). The two layers were separated at 70–80° C. and the lower layer was extracted twice more with methylcyclohexane (300 g). The yield of 4,6-dichloropyrimidine was 30.2 g (89.5%).

The lower layer was returned to the reactor and phosphorus pentachloride (89.6 g) was added. The procedure of the first paragraph of this Example was repeated using 4,6-dihydroxypyrimidine (50 g) and Hünigs base (114 g). The reaction mixture was extracted in the same way but 3×600 g aliquots of methylcyclohexane were used. The yield of 4,6-dichloropyrimidine was 42.92 g (64%).

Half of the lower layer was returned to the reactor and phosphorus pentachloride (89.6 g) was added. The procedure of the first paragraph of this Example was repeated using 4,6-dihydroxypyrimidine (50 g) and Hünigs base (114 g). The reaction mixture was extracted in the same way but 3×600 g aliquots of methylcyclohexane were used. The yield of 4,6-dichloropyrimidine was 34.87 g.

EXAMPLE 14

Using the process conditions of the first paragraph of Example 13 4,6-dihydroxypyrimidine (10 g), phosphorus oxychloride (29.84 g) and Hünig's base (22.8 g) were contacted. Thirty minutes after the addition of Hünig's base had been completed phosphorus pentachloride (37.2 g) was added. More 4,6-dihydroxypyrimidine (20 g) and Hünig's base (45.6 g) were added and the resulting mixture was stirred for 30 minutes. Phorphorus pentachloride (74.4 g) was added after which 4,6-dihydroxypyrimidine (40 g) and Hünig's base (91.2 g) were added. The resulting mixture was stirred at 70–75° C. for 2.5 hours and then extracted with methylcyclohexane (3×300 g). The extracts were combined, washed with aqueous sodium bicarbonate solution and then with water. The solvent was distilled to leave 4,6-dichloropyrimidine as a white solid (45.2 g, 42.6%). The methylcyclohexane distillates contained a further amount of 4,6-dichloropyrimidine (14.5 g, 16%).

CHEMICAL FORMULAE
(IN DESCRIPTION)

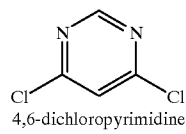
4,6-dichloropyrimidine (2)

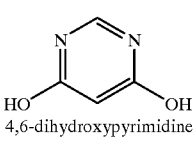
4,6-dihydroxypyrimidine (1)

POCl$_3$ phosphorus oxychloride

COCl$_2$ phosgene

-continued

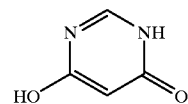
(A)

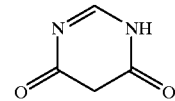
(B)

We claim:

1. A process for preparing 4,6-dichloropyrimidine comprising treating 4,6-dihydroxypyrimidine with phosphorus oxychloride in the presence of a saturated hindered amine, the hydrochloride salt of a saturated hindered amine, or an unsaturated 5-membered nitrogen containing ring or a mixture thereof, and, as a first step, directly extracting with a solvent the 4,6-dichloropyrimidine so formed from the liquid reaction mixture by means of a counter-current liquid-liquid separation technique.

2. A process as claimed in claim 1 wherein the 4,6-dichloropyrimidine so formed is directly extracted by a solvent which is a saturated $C_{5-7}$ straight or branched chain alkane or an unsubstituted or alkyl substituted $C_{5-7}$ cycloalkane.

3. A process as claimed in claim 1 wherein the residue remaining after directly extracting the 4,6-dichloropyrimidine is mixed with an aqueous solution of sodium or potassium hydroxide to liberate the saturated hindered amine or unsaturated 5-member nitrogen containing ring or mixture thereof used in the process.

4. A process for preparing 4,6-dichloropyrimidine as claimed in claim 1 comprising treating 4,6-dihydroxypyrimidine with phosphorus oxychloride in the presence of either a saturated tertiary amine or a 5-membered nitrogen containing ring or a mixture thereof.

5. A process as claimed in claim 1 comprising treating 4,6-dihydroxypyrimidine with phosphorus oxychloride in the presence of N,N-diisopropylethylamine ($(CH_3)_2CH)_2(CH_3CH_2)N$.

6. A process as claimed in claim 1 wherein the molar ratio of 4,6-dihydroxypyrimidine:phosphorus oxychloride:saturated hindered amine or saturated hindered amine hydrochloride is in the range (0.8–1.2):(2–2.5):(1.8–2.2).

7. A process as claimed in claim 5 comprising adding 4,6-dihydroxypyrimidine to a mixture of N,N-diisopropylethylamine and phosphorus oxychloride.

8. A process as claimed in claim 5 comprising adding N,N-diisopropylethylamine to a mixture of 4,6-dihydroxypyrimidine and phosphorus oxychloride.

9. A process as claimed in claim 1 comprising the steps: (a) treating 4,6-dihydroxypyrimidine with phosphorus oxychloride in the presence of a saturated hindered amine, a saturated hindered amine hydrochloride or an unsaturated 5-membered nitrogen containing ring or a mixture thereof; (b) separating 4,6-dichloropyrimidine from the reaction mixture; and, (c) treating the residue so formed with either phosphorus pentachloride or a mixture of phosphorus trichloride and chlorine.

10. A process as claimed in claim 1 comprising the steps: (a) treating 4,6-dihydroxypyrimidine with phosphorus oxychloride in the presence of a saturated hindered amine, a saturated hindered amine hydrochloride or an unsaturated 5-membered nitrogen containing ring or a mixture thereof; (b) treating the mixture formed in step (a) with either phosphorus pentachloride or a mixture of phosphorus trichloride and chlorine; (c) adding 4,6-dihydroxypyrimidine and a saturated hindered amine, a saturated hindered amine hydrochloride or an unsaturated 5-membered nitrogen containing ring or a mixture thereof to the mixture formed in step (b); (d) optionally repeating steps (b) and (c) once more or two or more times; and (e) separating 4,6-dichloropyrimidine from the reaction mixture.

11. A process as claimed in claim 1 in which less than one equivalent of phosphorus oxychloride is used in the reaction mixture initially, and either phosphorus pentachloride or a mixture of phosphorus trichloride and chlorine is added during the process to regenerate phosphorus oxychloride.

* * * * *